United States Patent
Conti et al.

(10) Patent No.: US 10,605,700 B2
(45) Date of Patent: Mar. 31, 2020

(54) FATIGUE TO FRACTURE MEDICAL DEVICE TESTING METHOD AND SYSTEM

(71) Applicant: DYNATEK LABS, INC., Galena, MO (US)

(72) Inventors: James C. Conti, Galena, MO (US); Elaine R. Strope, Galena, MO (US); Christopher Strope Conti, Galena, MO (US)

(73) Assignee: DYNATEK LABS, INC., Galena, MO (US)

( * ) Notice: Subject to any disclaimer, the term of this patent is extended or adjusted under 35 U.S.C. 154(b) by 0 days.

(21) Appl. No.: 16/419,549

(22) Filed: May 22, 2019

(65) Prior Publication Data

US 2019/0339168 A1   Nov. 7, 2019

Related U.S. Application Data

(63) Continuation of application No. 15/424,689, filed on Feb. 3, 2017.

(Continued)

(51) Int. Cl.
*G01M 99/00* (2011.01)
*A61F 2/24* (2006.01)
*A61F 2/90* (2013.01)

(52) U.S. Cl.
CPC ......... *G01M 99/007* (2013.01); *A61F 2/2418* (2013.01); *A61F 2/2472* (2013.01); *A61F 2/90* (2013.01)

(58) Field of Classification Search
CPC ..... G01M 99/00; A61F 2/07; A61F 2240/008; A61F 2/82; A61F 2/06; A61F 2/2472; G01N 2203/0222; G01N 3/12; G01N 2203/0048; G01N 2203/027; G01N 3/32; G01N 2203/0073; G01N 2203/0005;
(Continued)

(56) References Cited

U.S. PATENT DOCUMENTS 5,670,708 A   9/1997   Vilendrer
6,810,751 B2   11/2004   Moreno et al.
(Continued)

OTHER PUBLICATIONS

"Gong et al. Fatigue to Fracture: An Informative, Fast, and Reliable Approach for Accessing Medical Implant Durability, 3 Journal of ASTM International, vol. 6, No. 7, Paper ID JAI102412, 10 pages".
(Continued)

*Primary Examiner* — Brandi N Hopkins
(74) *Attorney, Agent, or Firm* — Kutak Rock LLP; James H. Jeffries

(57) ABSTRACT

A method of determining the endurance limit of an implantable medical device is disclosed. The method utilizes a mock vessel that has a compliance that is higher or lower than the normal compliance of a human vessel for which the device is to be used. The device is deployed into the mock vessel and a curable liquid is used to form a layer over the device on the surface of the lumen of the mock vessel. High pressure pulsatile pressurization is applied to the lumen of the mock vessel to cause a failure of the implantable medical device. The amount and cycles of pressure necessary to cause a failure may be used to determine the endurance limit of the implantable medical device.

20 Claims, 7 Drawing Sheets

Related U.S. Application Data

(60) Provisional application No. 62/291,192, filed on Feb. 4, 2016.

(58) Field of Classification Search
CPC ....... G01N 2203/02566; Y10S 623/912; Y10S 623/913
See application file for complete search history.

(56) References Cited

U.S. PATENT DOCUMENTS

| | | |
|---|---|---|
| 7,254,988 B2 | 8/2007 | Keeble |
| 7,363,821 B2 | 4/2008 | Black et al. |
| 7,621,192 B2 | 11/2009 | Conti et al. |
| 8,196,478 B2 | 6/2012 | Lorenz et al. |
| 8,490,504 B2 * | 7/2013 | Weinberg .................. G01N 3/36 73/760 |
| 9,417,110 B2 * | 8/2016 | Raz ..................... G01M 99/007 |
| 2003/0110830 A1 | 6/2003 | Dehdashtian et al. |
| 2003/0125804 A1 | 7/2003 | Kruse et al. |
| 2010/0225478 A1 * | 9/2010 | McCloskey .............. G01N 3/32 340/540 |
| 2017/0227426 A1 * | 8/2017 | Conti .................. G01M 99/007 |

OTHER PUBLICATIONS

"Kemp et al. Instron Medical Device and Biomaterials Markets, Testing of Stents and Stent Materials, pp. 1-4".

"Non Final Office Action Received for U.S. Appl. No. 15/424,689, dated Jan. 24, 2019, 17 pages".

"Pitney et al.. Longitudinal Stent Deformation: Important of Stent Type and Stent Apposition, American Journal of 2 Biomedical Engineering 2013, 3(3): pp. 63-69."

\* cited by examiner

FATIGUE TO FRACTURE MEDICAL DEVICE TESTING METHOD AND SYSTEM

CROSS-REFERENCE TO RELATED APPLICATIONS

This application is a continuation of and claims the benefit of U.S. patent application Ser. No. 15/424,689 filed Feb. 3, 2017, which claimed the benefit of U.S. Patent Application Ser. No. 62/291,192 filed Feb. 4, 2016, the disclosures of which are incorporated herein by reference.

BACKGROUND

The invention generally relates to systems and methods for fatigue or stress testing to fracture one or more implantable medical devices such as the mesh grid tubes used for implantable medical stents. More specifically, the invention relates to systems and methods for stressing a stent or mesh tube to fracture or break which provides valuable data for estimating the usable life of such devices.

Modern medical procedures routinely include the employment of implantable devices into a patient's vascular system to perform various therapeutic functions. Prosthetic vascular implants, such as heart-valves, stents, grafts, mesh tubes, and stent-grafts used for human implantation are subjected to the continuous fluctuating stress of blood pressure. As an example, tubular mesh samples or stents are often inserted in an artery of a patient to maintain a flow lumen through the artery at a location that had previously been at least partially blocked or occluded. It is therefore necessary to test such implants to prove their durability over a lifetime of exposure to pulsatile blood pressure. Ideally such stents, mesh samples, or other vascular prostheses, are able to withstand the physiological dynamics that occur within the vessel or organ in which they are emplaced. For instance, in the abdominal aorta, blood pressure in the average healthy subject is 120 mm Hg/80 mm Hg, i.e. the blood pressure varies by 40 mm Hg for every pulse. Compliance of a healthy aorta can be of the order of 20-25% per 100 mm Hg so that a change in vasculature diameter of 8 to 10% can be expected at every heartbeat. In order to simulate such a change in diameter, testers employ a pulse pressure between 80 mm Hg and 100 mm Hg. The vessel (artery, vein, etc) in the human body where an implantable medical device is to be implanted is referred to as the target human vessel.

One widely used methodology of testing implantable medical devices is referred to as "testing-to-success". Typically, in testing-to-success, vascular implants are tested for 400,000,000 cycles which represent approximately 10 years of implantation life at a heart rate of 80 beats per minute. Testing-to-success is indicative of the durability of the stent under physiological conditions of systolic/diastolic pressures encountered in accelerated radial pulsatile durability testing. However, testing-to-success does not predict the endurance limit or fatigue life of the stent or other implantable device, i.e., there is no way to know under what conditions, including conditions that may exceed physiological parameters, the stent or stent graft would fail. The endurance limit, also referred to as the fatigue limit, is a well-known concept in stress testing and materials science.

To address this weakness in the "testing-to-success" methodology, new regulations (FDA, ASTM, ISO) are being developed that outline test requirements that are now concerned with predicting fatigue limits of the stent or stent graft and require stent manufacturers to test their products under a 'testing to failure' or 'test to fracture' regime, so that stents and stent grafts may be tested up to their endurance limit. An alternative method that is being rapidly pursued and evaluated is a "fatigue-to-fracture" approach. This testing methodology involves a combination of finite element analysis modeling and in vitro testing to assess the durability of stents or other implantable through established fracture mechanics techniques, such as use of a Wöhler curve, to identify the endurance/fatigue limit of a device. These testing guidelines and standards are still under development, i.e. ASTM F04.30.06.

Knowing when and where fracture, secondary fracture, or other failure, of the stent, mesh tubes, or other prosthesis, is most likely to occur under a variety of simulations is ideal to device development. Manufacturers can then use this information to redesign their product with the knowledge gained by fatigue to fracture analysis. The occurrence of the foregoing described fracture or other failure is referred to herein as a failure event. Providing a stent, or other prosthesis, of suitable strength and durability for lasting implantation into a patient, to minimize the likelihood of failure is desirable. Determining the fatigue and endurance limits of the stent, or other prosthesis, helps accomplish the provision of a suitable stent, or other prosthesis.

SUMMARY OF THE INVENTION

Other objects and advantages of this invention will become apparent from the following description taken in conjunction with the accompanying drawings wherein are set forth, by way of illustration and example, certain embodiments of this invention.

In accordance with the present invention, a vascular prosthesis tester for inducing mechanical stresses upon a vascular prosthesis having a tubular channel, or lumen, extending along a longitudinal axis is provided.

In one embodiment, a method for testing fatigue to fracture by means of enhanced radial compression of a tubular mesh medical implant comprises the steps of: providing a mock vessel that has a lower than normal compliance; deploying the medical implant within the mock vessel; loading the mock vessel and implant into a testing unit; repeatedly expanding the mock vessel and medical implant therewithin using a pressurized fluid; providing a high speed camera to monitor the deflection of the test sample by direct visualization of the medical implant to ascertain the time of initial failure or fracture. It is foreseen that the testing unit controls at least one of the following parameters: temperature, pH, frequency of pulsation of the pressurized fluid, minimum pressure, and maximum pressure.

The preferred compliance of the mock vessel in this method may be between 1% and 2% per 100 mm Hg. It is foreseen that the pressurized fluid is at least one of air, a saline solution, or distilled water. The frequency of expansion of the mock vessel and medical implant may be between 1 to 150 Hz but more preferably between 20 and 40 Hz for optimal testing of a typical implantable vasculature stent.

In one embodiment, the implant is a vascular graft or endovascular prosthesis or common mesh stent with an internal diameter from 2 to 50 mm.

In another embodiment of the invention, a method for testing fatigue to fracture by radial expansion of a medical implant comprises the steps of: providing a mock vessel that has a higher than normal compliance; positioning a tubular medical implant over the mock vessel; loading the mock vessel and implant into a testing unit; repeatedly expanding the mock vessel and medical implant from within using a pressurized fluid; providing a high speed camera to monitor the deflection of the test sample by directly visualization of the medical implant to ascertain the time of initial failure or fracture.

In yet another embodiment, the medical implant fatigue is tested using a combination of enhanced radial compression and enhanced radial expansion. The combination testing comprises the steps of providing a mock vessel having lower than normal compliance; positioning a tubular medical implant within the mock vessel; placing an inner liner tube within the mock vessel to substantially capture the tubular medical implant between the outer periphery of the inner liner tube and the inner wall of the mock vessel; loading the mock vessel, implant and inner liner tube into a testing unit; repeatedly expanding the mock vessel and medical implant from within the inner liner tube from within using a pressurized fluid; providing a high speed camera to monitor the deflection of the test sample by directly visualization of the medical implant to ascertain the time of initial failure or fracture. The first inner liner tube may have an outer diameter that is from between 85% to 95% of an inner diameter of the mock vessel.

In another embodiment, the inner liner tube is made from a liquid plastic, such as silicone, that has been cured within the mock vessel to substantially encapsulate the medical implant.

DETAILED DESCRIPTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the components of the invention in actual use.

Figure 1:
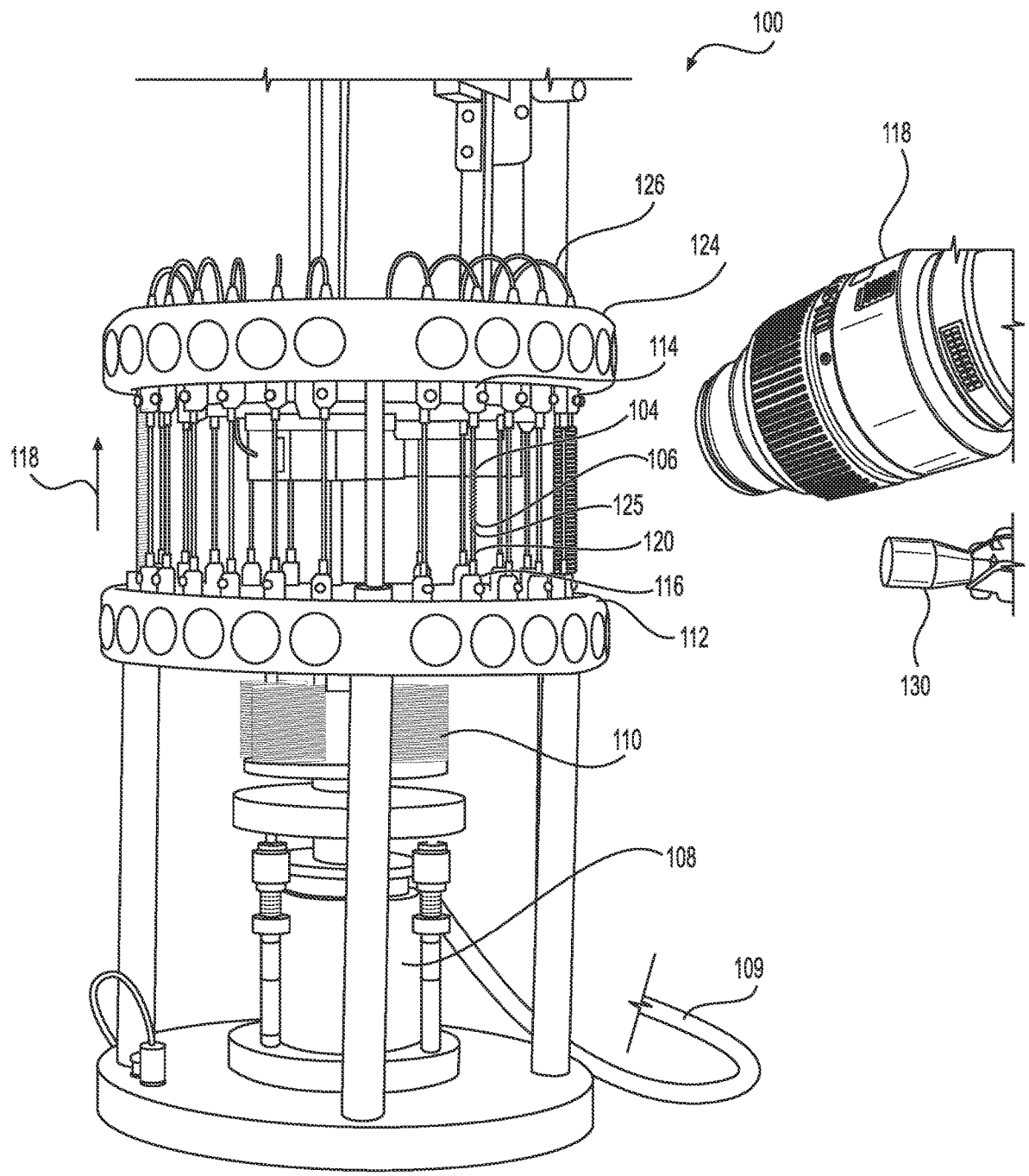
FIG. 1 is a top perspective view illustrating a durability test apparatus for fatigue to fracture according to the present invention.

Referring to FIG. 1, the reference numeral 100 generally designates a fatigue to fracture test apparatus according to the present invention. The fatigue to fracture test apparatus 100 having one or more in-line conduits for attachment to mock vessels or vascular grafts 106. The mock vessel or conduit 106 will have a compliance or measure of the distensibility of a chamber expressed as a change in volume per unit change in pressure. A normal arterial compliance varies greatly anywhere from approximately 4-5% per hundred millimeters (mm) of Mercury (Hg) in the smaller arteries and up to 20-30% per hundred millimeters (mm) of Mercury (Hg) in the ascending aorta. It is foreseen that the mock vessels 106 may be made from silicone, Teflon®, Fluorinated Ethlene Propylene, PerfluoroAlkoxy, Tygon®, PharmaPure®, Kynar, or other known fluid handling tubing. It is foreseen that these mock vessels 106 can be straight, curved, undulated, or bifurcated, and are made to virtually any range of compliance for radial testing of stents.

An implantable medical device 104, such as a stent or mesh tube, is deployed in the mock vessel 106, which in some cases may be referred to as a mock artery, along a longitudinal axis A. A vascular stent-type implantable medical device 104 is a small tubular structure commonly made of a thin layer of one of a few biocompatible and corrosion resistant metals, such as 316L stainless steel, nitinol, or cobalt-based alloys usually in a crossed lattice like or mesh 106 pattern. Stents have unique attributes that influence the assessment of their durability. First, the overall size of the stent can be quite small; some coronary stents are less than 2.5 mm in diameter and 10 mm in length. Typical cross-sectional dimensions of a single strut, the fundamental structural unit that forms the stent, are on the order of 0.11 mm2. The stent 104 is deployed by compression, so that they can be delivered into the artery, for example, down to less than 1 mm in diameter. After being delivered to the location of interest in the mock vessel 106, one of two techniques can be used to expand the stent-type implantable medical device 104 to its clinically relevant diameter. The first is to use a self-expanding stent 104 made of Nitinol (Nickel Titanium) which will expand to a predefined diameter. The second technique is to use a balloon to expand the stent-type implantable medical device 104 to the indicated diameter. In either case the stent-type implantable medical devices 104 are designed to expand to 110% of the inside diameter of the mock vessel 106 at the point of highest blood pressure. This is done to ensure that the stent-type implantable medical devices 104 do not migrate during the systolic portion of the heartbeat.

A motor or drive 108 moves fluid, such as saline, from the fluid inlet 109 to the pump 110 by the action of metal bellows, rolling rubber bellows, a piston or the like. Motor 108 may include, for example, a hydraulic, electrodynamic, AC or servo drive system. The pump 110 may accelerate test conditions where, for example, when testing success, 400 million heartbeats may be replicated at a cycle rate ranging from about 50-6000 cycles/minute. It is foreseen that testing fatigue to fracture can be done at physiological speeds between 1-2 Hz or at accelerated speeds between 40 Hz and 60 Hz, but for faster results as according to the present invention, testing can be done at accelerated speeds and high pressures such as 50 pounds per square inch (psi) or approximately 2500 mmHg. The use of higher pressure in the mock vessel then exist in a physiological context is also referred to as hyper-physiological loading conditions.

From pump 110, fluid moves through manifold 112, where pressures being delivered to devices 104 are monitored. To simulate blood flow, the pressurized test fluid is delivered in a pulsatile flow, with pressures modulated between specific points to mimic systolic and diastolic pressures. Manifold 112 may contain stopcocks or isolation valves (not shown) that allow mock vessels 106 and devices 104 to be isolated, removed, replaced, and/or inspected without draining the entire apparatus 100. The manifold 112 allows test fluid to be pumped through all samples in a closed loop, ensuring an even temperature and pressure distribution within all mock vessels 106 and also ensuring the removal of shed particles.

Stopcocks 114 may be disposed downstream of mock vessels 106 to allow the user to select which mock vessels 106 are open and which are closed. Check valves 116, also known as bleed valves or one-way valves, allow fluid to flow along the path shown by arrow 118, while inhibiting or preventing backflow during diastole of pump 110 when a pulsatile flow is used for testing. Check valves 116 also help to control the rate of flow through elastomeric tubing 120. A tank (not shown), containing implantable device 104, mock vessels 106, stopcocks 114, check valves 116 and tubing 120, may be filled with a heated liquid (not shown), for example, to simulate body temperature. It is also foreseen that the test fluid exits elastomeric tubing 120 through manifold 124 and is carried outward for further processing by tubing 126.

To evaluate the fatigue to fracture, high speed photographic verification of stent fatigue by means of a camera 118 and optional external light source 130, such as a FastCam PCI 1280, is utilized. The inside wall 123 of the mock vessel 106 may be marked with predetermined sets of points (not shown) and the outside surface 125 may be marked with a second predetermined set of points, to create landmarks on the vessel 106 that can be tracked by the camera 118 during pulsation. When used, the high speed camera 118 will track the first and second predetermined sets of points or landmarks on the stent-type implantable medical device 104 and the distance between the marks will change as the mock vessel 106 expands and contracts. The high speed camera 118 constitutes a method of direct observation and direct measurement of the stent-type implantable medical device. In the alternative, landmarks may be identified on the stent-type implantable medical device 104 itself.

It is foreseen that laser micrometer (not shown) measurements may also be added and appropriate to monitor the operating conditions of the test.

It will be appreciated that FIG. 1 teaches by way of example and not limitation. The number of system components may be increased or decreased with respect to what is shown. In one such example, sensors (not shown) providing optional alarm capabilities for temperature, pH, mean pressure, pulsatile pressure, number of cycles, and speed may be incorporated into apparatus 100.

Figure 2:
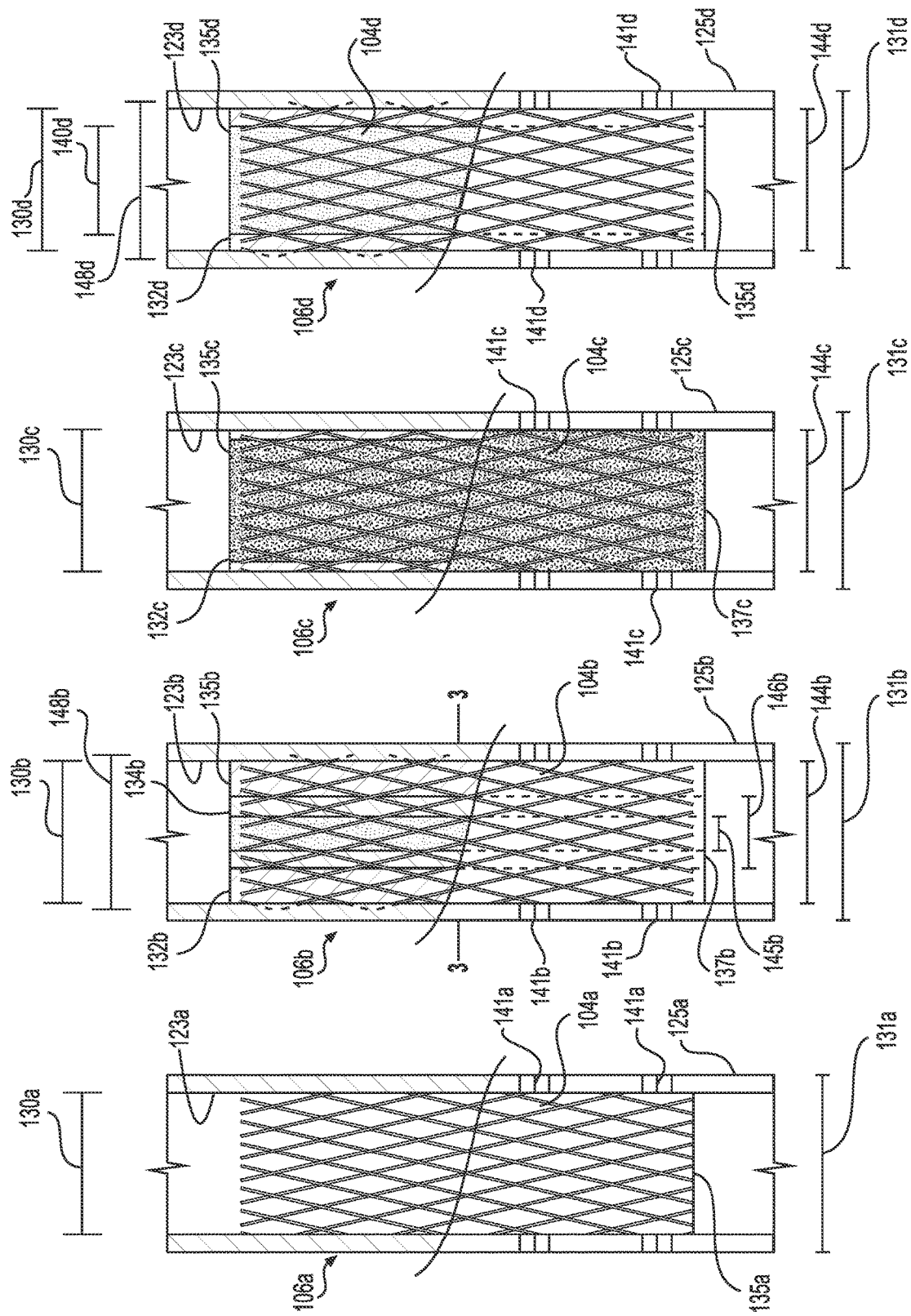
FIG. 2A is an enlarged side view of FIG. 1 with portions cut away illustrating a first embodiment of the present invention, wherein a mock artery has lower than normal compliance and a mesh stent loaded within the mock artery.
FIG. 2B is an enlarged side view of FIG. 1 with portions cut away illustrating a second embodiment of the present invention, wherein a mock artery has a normal compliance with a mesh stent having first and second inner liners deployed within.
FIG. 2C is an enlarged side view of FIG. 1 with portions cut away illustrating a third embodiment of the present invention, wherein a mock artery has a normal compliance with a mesh stent loaded having an inner liner made from silicone.
FIG. 2D is an enlarged side view of FIG. 1 with portions cut away illustrating a fourth embodiment of the present invention, wherein a mock artery has a lower normal compliance with a mesh stent loaded having an inner liner.

Enhanced Radial Compression Testing: Referring now to FIG. 2A, a mock vessel 106a is shown with outer diameter 131a. The mock vessel 106a has a lower than normal compliance, which varies likewise to the purpose of the stent-type implantable medical device 104a to be tested. The mock vessel may have set points 141a marked on the outer surface 125a of the mock vessel, to be used with the camera to provide reference points for visualizing fracture of the stent-type implantable medical device 104a. The points 141a may be between the end 135a of the device 104a and the opposing end of the device 104a. It is desirable that the inner surface of mock vessel 106a will have an inner diameter 130a in the range of 5%-35% greater than the outer diameter of the stent-type implantable medical device 104a and between 1-2% change in radius per 100 mm of mercury (Hg). Because of the very low compliance of the mock vessel 106a, the stent-type implantable medical device 104a will be restrained by the vessel wall from expanding to the designed amount which puts the stent 104a under compressive forces faster than under normal compliance conditions. Stent-type implantable medical devices 104a are typically designed to expand to 110% of the inside diameter of an artery (not shown) at the point of highest blood pressure, herein illustrated in test situations with a mock vessel 106a. This is done to ensure that the stents do not migrate during the systolic portion of the heartbeat. The low compliance mock vessel 106a creates an overload situation wherein radial compression forces are introduced when high pressure is used to open up and on recoil deliver another high pressure load to the stent-type implantable medical device 104a. The repetitive compressive pressure associate with the pulsatile flow through the mock vessel 106a causes greater than normal stress on the stent-type implantable medical device 104a and under controlled conditions the stent-type implantable medical device 104a can be forced to fail. Testing has shown that failure may originate at an apex of the stent-type implantable medical device 104a. Once failure occurs at a single point of the stent, complete failure may follow quickly, commonly with the mesh stent "unzipping" along a linear path originating at the original point of failure.

Enhanced Radial Expansion Testing: Referring now to FIG. 2B, a mock vessel 106b with inner surface 123b and outer diameter 131b is shown. The mock vessel 106b has a higher than normal compliance, (i.e. inner diameter 130b of mock vessel 106b is greater than 130a under fatigue to fracture testing pressures) which varies likewise to the purpose of the stent-type implantable medical device 104b being tested. The mock vessel may have set points 141b marked on the outer surface 125b of the mock vessel, to be used with the camera to track fracture of the stent-type implantable medical device 104b. In some embodiments, the testing configuration for the stent-type implantable medical device 104b includes an inner liner 132b. In some embodiments, the inner liner 132b is a thin walled tube inserted through the stent-type implantable medical device 104b after the stent 104b has been expanded. It is foreseen that the stent-type implantable medical device 104b may be expanded by either a balloon or is made of a self-expanding material such as Nitinol. It is preferred that the inner liner 132b may be made of several additional series of layers, and it is not meant to be limited. In some embodiments, liquid pressurization of the mock vessel 106b creates an inner radial expansive pressure or force that embeds the stent 104b into the mock vessel 106b as seen in FIG. 2B. In some embodiments, the inner liners 132b may be created by coating the inner surface of the mock vessel 106 and stent-type implantable medical device 106b with liquid silicone to create the inner liner 132b. The thickness of the liner 132b can be controlled by the length and number of applications of liquid silicone. When dried, the silicone substantially encapsulates the test stent 104b to simulate endothelialzation of the stent-type implantable medical device.

The ends 135b and 137b of the inner liner stick out further than a length of the stent-type implantable medical device 104b. It is preferred that extra dips of silicone (not shown) may be formed on the ends 135b of the inner liner 132b. In the alternative, sleeves may be formed from low compliant tubing and placed over the ends 135b of the inner liner 132b.

Figure 3:
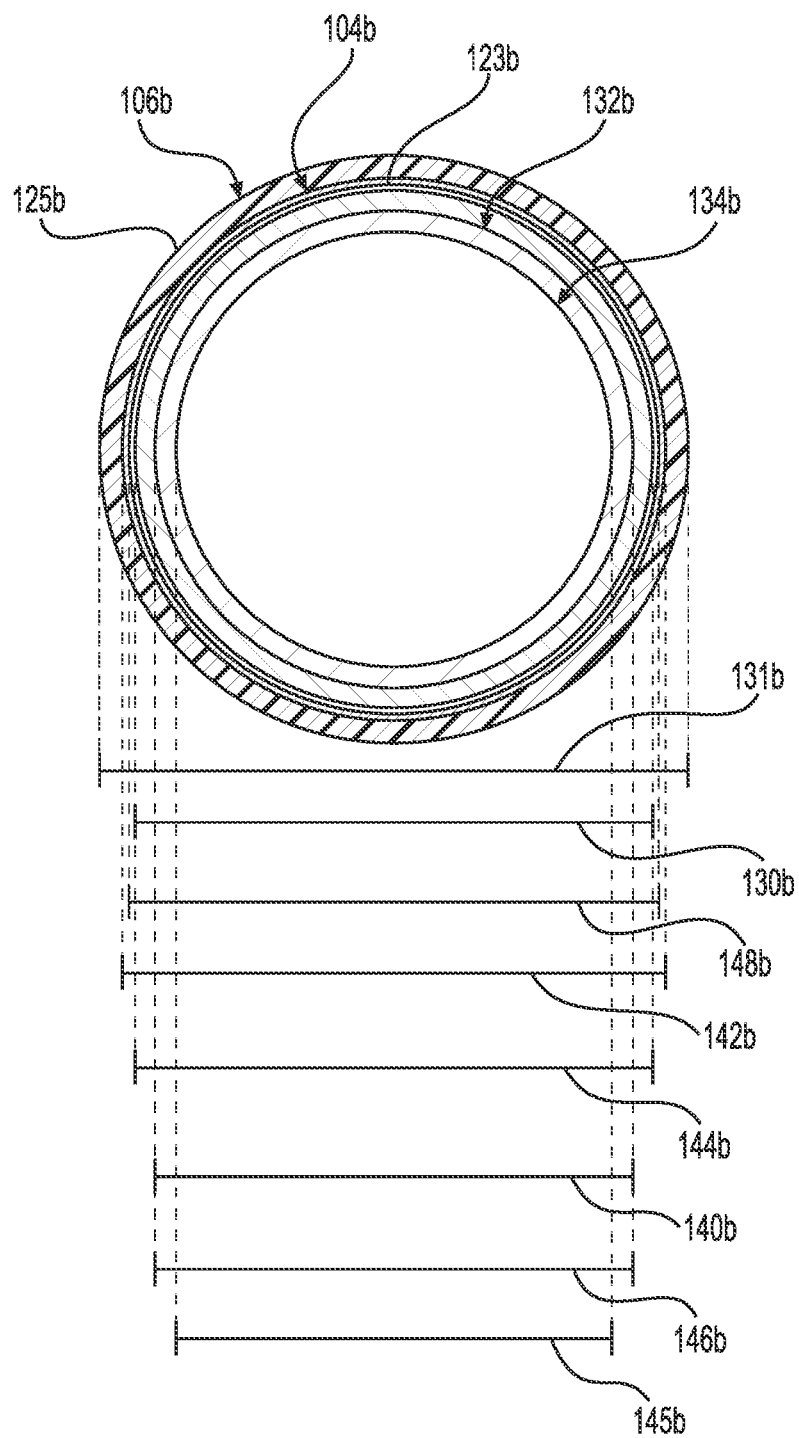
FIG. 3 is a cross section view of FIG. 2B taken along the line 3-3.

Referring to FIG. 3, a cross-sectional view of mock vessel 106b is depicted along the axis 3-3 shown on FIG. 2B. Mock vessel 106b has an outer diameter 131b and an inner surface 123b with inner diameter 130b. The mock vessel 106b is shown with a stent-type implantable medical device 104b, an inner liner 132b, and a second inner liner 134b. The inner line 132b has an inner diameter 140b and an outer diameter of 144b. The inner liner 134b has an inner diameter of 145b and an outer diameter of 146b. In some embodiments, the inner liner 132b will have an inner diameter 140b in the range of ½ to ⅔ the outer diameter 148b of the stent-type implantable medical device 104b or between 1-5% change in radius per 100 mm of mercury (Hg) compliance. The inner liner 132b will have an outer diameter 144b that is 90% of the working inner diameter 148b of the stent-type implantable medical device 104a. The stent-type implantable medical device 104a will be forced to expand to the inner diameter 130b of the mock vessel 106b because of the very high compliance of the inner liners 132b, 134b, which places the stent-type implantable medical device 104b under expansive forces faster than under normal compliance conditions. The high compliance inner liner 132b creates an overload condition, as the expansion test requires high pressure or high frequency pulsatile flow to open up the stent-type implantable medical device 104b and on recoil deliver a high load to the stent-type implantable medical device 104b. The mock vessel 106b may have set points 141b marked on the outer surface 125b of the mock vessel 106b, to be used with the camera to track fracture of the stent-type implantable medical device 104b.

Referring now to FIG. 2C, a mock vessel 106c is shown with inner diameter 130c and outer diameter 131c. The mock vessel 106c has a higher than normal compliance, which varies likewise to the purpose of the stent-type implantable medical device 104c being tested. The mock vessel 106c may have set points 141c marked on the outer surface 125c of the mock vessel, to be used with the camera to track fracture of the stent-type implantable medical device 104c. The stent-type implantable medical device 104c further includes an inner liner 152 made from cured liquid silicone. The inner liner 132c has ends 135c and 137c and an outer diameter 144c. The mock vessel 106c containing the expanded stent-type medical device 104c is removed from the tester 100 and filled with liquid silicone. The liquid silicone sticks to the stent-type implantable medical device 104c and inner wall 123c of the mock vessel 106c and may be allowed to drip out of the mock vessel 106c to leave a thin layer of silicone behind. The area where the stent-type implantable medical device 104c is deployed is cured to harden the silicone creating the inner liner 132c. It is foreseen that the inner liner 132c may be made of several additional series of layers of silicone, by repeating this process, and it is not meant to be a limiting example. The inner liner 132c, like the inner liner 132b explained above, creates an inner radial expansive pressure or force that embeds the stent-type implantable medical device 104c into the mock vessel 106c. The inner liner liquid may be a silicone based material, but may also be selected from other materials such as Teflon®, Fluorinated Ethlene Propylene, PerfluoroAlkoxy, Tygon®, PharmaPure®, Kynar, or other known fluids that are capable of hardening into a flexible liner.

Combination Enhanced Radial Compression and Enhanced Radial Expansion Testing: Referring now to FIG. 2D, a configuration is depicted for generating a combination of compressive and expansive forces to be imparted on the stent-type implantable medical device 104d. A mock vessel 106d with inner diameter 123d and outer diameter 131d is shown with a lower than normal compliance, which varies likewise to the purpose of the stent-type implantable medical device 104d. The mock vessel 106d may have set points 141d marked on the outer surface 125d of the mock vessel, to be used with the camera to track fracture of the stent-type implantable medical device 104d. It is preferred that the mock vessel 106d will have an inner diameter 130d in the range of ½ to ⅔ the outer diameter 131d of the stent-type implantable medical device 104d or between 1-2% change in radius per 100 mm of mercury (Hg), and because of the very low compliance of the mock vessel 106d, the stent-type implantable medical device 104d will not always expand to the designed amount which places the stent-type implantable medical device 104d under compressive forces faster than under normal compliance conditions. After the stent-type implantable medical device 104d is positioned within the mock vessel 106d an inner liner 132d is placed therewithin to capture the stent 104d between the outer wall of the inner liner 132d and the inner wall of the test vessel. The inner liner 132d may be a thin walled tube inserted through the stent-type implantable medical device 104d. In some embodiments, the inner liner 132d will have an inner diameter 140d in the range of ½ to ⅔ the diameter 148d of the stent-type implantable medical device 104d or between 1-5% change in radius per 100 mm of mercury (Hg) compliance. The ends 135d of the inner liner 132d extend beyond the ends of stent-type implantable medical device 104d. The outer diameter 144d of the inner liner 132d may between 85-95% of the working inner diameter 148d of the stent-type implantable medical device 104d. The stent-type implantable medical device 104d will be forced to expand to the inner diameter 130d of the mock vessel 106d because of the very high compliance of the inner liner 132d which places the stent-type implantable medical device 104d under expansive forces upon application of the pressurized test liquid. The high compliance inner liner 132d in combination with the low compliance mock vessel 106d create an overload condition, as the expansion/compression test requires high pressure or high frequency pulsatile flow to open up the stent-type implantable medical device 104d and on recoil deliver a high compression load to the stent-type implantable medical device 104d. Repeated compression and expansive force imparted on the stent-type implantable medical device 104a during pulsatile flow may embed the stent-type implantable medical device 104d to the mock vessel 106d, as is seen in FIG. 2D.

Figure 4:
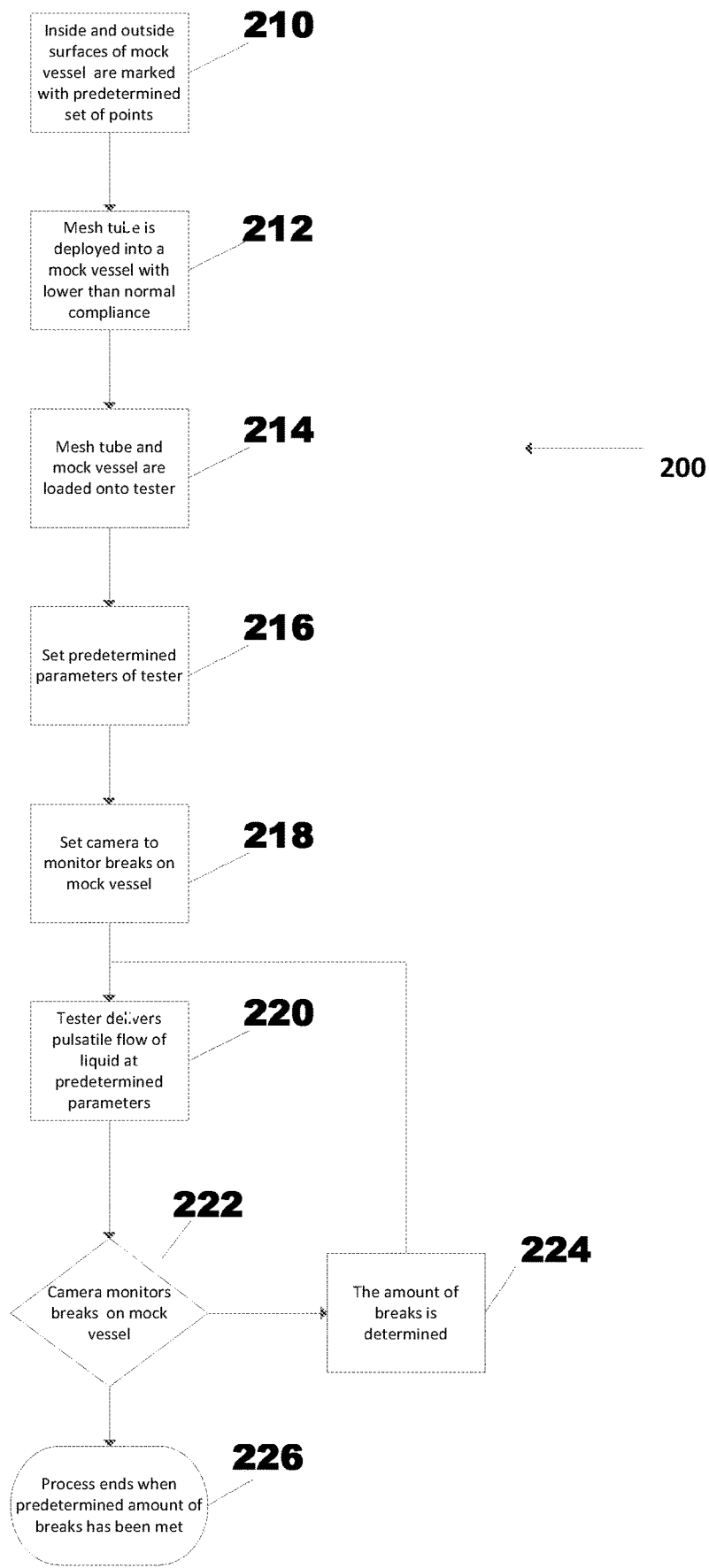
FIG. 4 is a flow diagram of a method in a first embodiment according to the present invention.

FIG. 4 is a flow diagram illustrating a method 200 of fatigue to fracture testing using radial compression. At step 210, the inside wall of the mock vessel is marked with predetermined sets of points and the outside wall is marked with a predetermined set of points, to create landmarks on the vessel that can be tracked by the camera during testing.

At step 212, a mesh tube, stent, or implantable sample is deployed in a mock vessel. The stent may be balloon expanded or made from Nitinol and is expanded as it is deployed. The mock vessel has a lower than normal compliance, i.e. 1% to 2% per 100 mm Hg. At step 214, the mesh tube and mock vessel as a unit are loaded onto a tester unit.

At step 216, the tester is set to deliver pulsatile flow including a predetermined: temperature, pH, pulsation frequency, and maximum and minimum pressure for each cycle.

At step 218, a high speed or still camera is set to monitor the deflection of the test sample. The high speed camera will track pairs of landmarks on the stent and the distance between the marks will change as the mock vessel expands and contracts. It is foreseen that a multitude of cameras may be necessary to give a full 360 degree view of the mesh tube.

At step 220, the tester is set to run at the predetermined parameters.

At step 222, when a break occurs, then at step 224, the number of cycles to break is determined, and the tester continues to run. When a predetermined number of breaks have been met, then process is ended at step 226. The whole method is repeated with adjusted parameters to generate the data necessary to determine fatigue properties of the tested stent.

Figure 5:
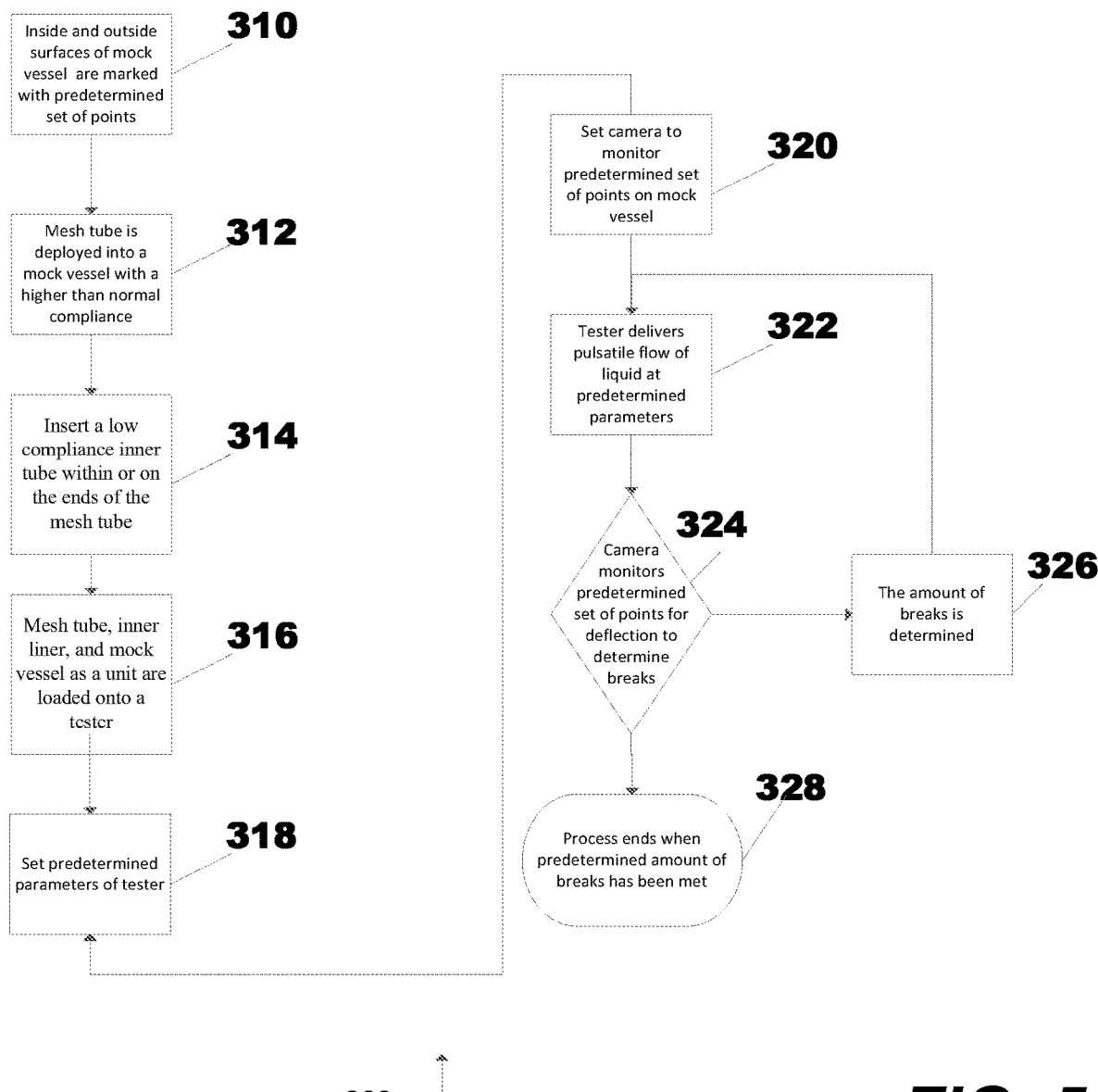
FIG. 5 is a flow diagram of a method in a first embodiment according to the present invention.

FIG. 5 is a flow diagram illustrating a method 300 of fatigue to fracture testing using radial expansion.

At step 312, a mesh tube, stent, or implantable sample is deployed onto a mock vessel. The stent may be balloon expanded or made from Nitinol and is expanded as it is deployed. The mock vessel has a higher than normal compliance for the test stent deployed.

At step 314, the test vessel has a radial compliance of 5% per 100 mm Hg and that has an outer diameter from between 85% to 95% a working inner diameter of the stent. The ends of the inner tube extending beyond the positioned stent may be strengthened by placing low compliance tubing over the ends or by applying a liquid silicone material to the ends of the test vessel, and then curing the silicone to harden.

At step 316, the mesh tube and mock vessel as a unit are loaded onto a tester unit.

At step 318, the tester is set to deliver pulsatile flow including a predetermined: temperature, pH, pulsation frequency, and maximum and minimum pressure for each cycle.

At step 320, a high speed or still camera is set to monitor the deflection of the test sample. The stent may have set points 141 marked on the outer surface or specific landmarks may be identified to be used with the camera to track fracture of the stent 104b. The high speed camera will track landmarks 141 on the stent and the distance between the marks 141 will change as the mock vessel expands, contracts, and fractures. A plurality of cameras may be necessary to give a full 360 degree view of the mesh tube.

At step 322, the tester is set to run at the predetermined parameters.

At step 324, when a break occurs then at step 326, the number of cycles to break is determined, and the tester continues to run. When a predetermined number of breaks have been met, then process is ended at step 328. The whole method is repeated with adjusted parameters to generate the data necessary to determine fatigue properties of the tested stent.

Figure 6:
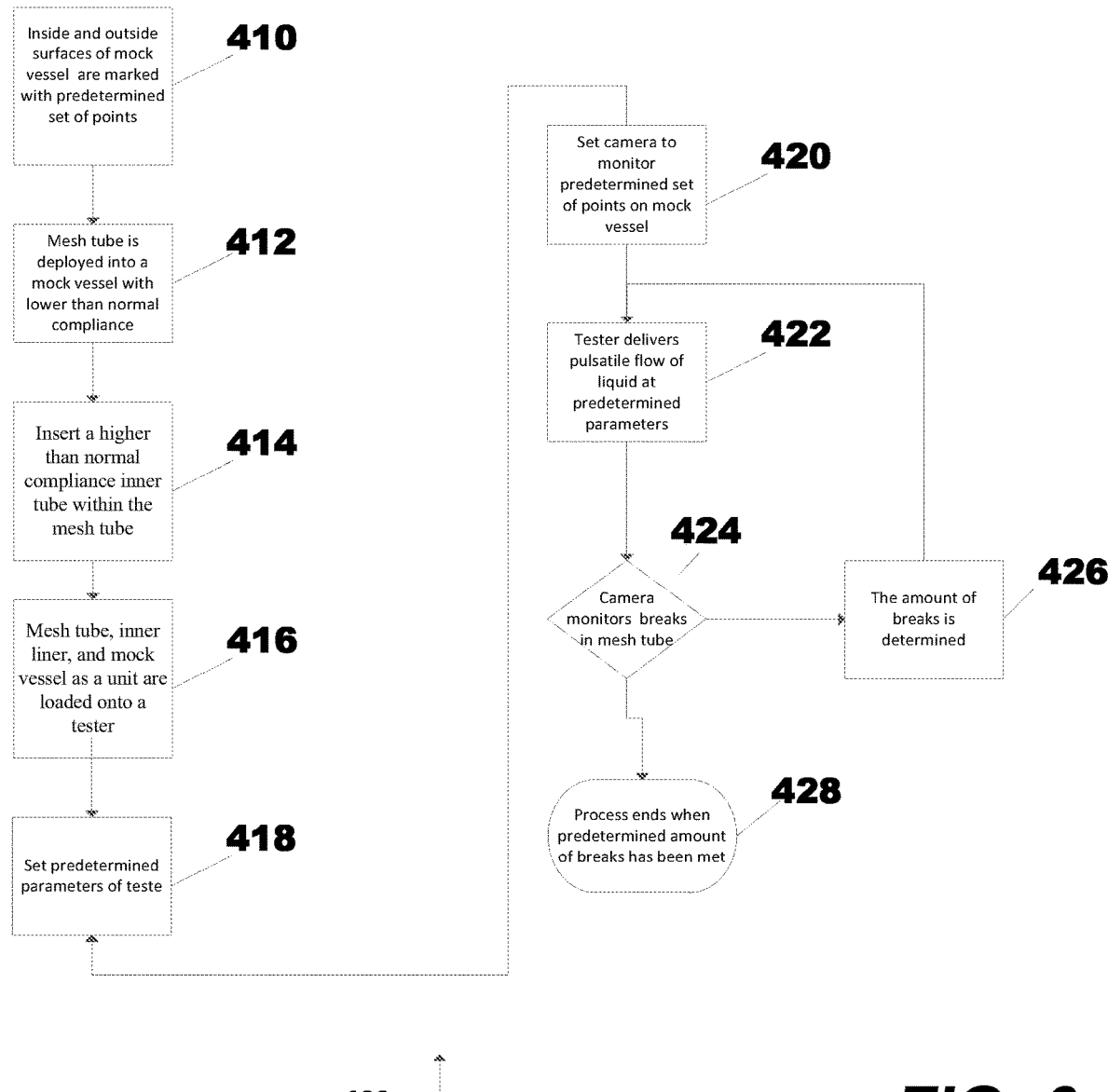
FIG. 6 is a flow diagram of a method in a first embodiment according to the present invention.

FIG. 6 is a flow diagram illustrating a method 400 of fatigue to fracture utilizing a combination of radial expansion and compression. At step 410, the inside wall of the mock vessel is marked with predetermined sets of points and the outside wall is marked with a predetermined set of points, to create landmarks on the vessel that can be tracked by the camera during testing.

At step 412, a mesh tube, stent, or implantable sample is deployed within a mock vessel. The stent may be balloon expanded or made from Nitinol and is expanded as it is deployed. The mock vessel has a lower than normal compliance for the test stent deployed, i.e. 1% to 2% per 100 mm Hg.

At step 414, insert a higher than normal compliance inner tube that has a radial compliance of 5% per 100 mm Hg and that has an outer diameter between 85-95% of the working inner diameter of the stent deployed. The inner tube may be formed by applying a liquid silicone material to the inner wall of the test vessel, and then curing the silicone to harden into an inner layer. The stent becomes encapsulated within the silicone-formed wall of the vessel.

At step 416, the mesh tube, inner liner, and mock vessel as a unit are loaded onto a tester unit.

At step 418, the tester is set to deliver pulsatile flow including a predetermined: temperature, pH, pulsation frequency, and maximum and minimum pressure for each cycle. Also, a predetermined number of breaks in the stent are set.

At step 420, a high speed or still camera is set to monitor the deflection of the test sample. The high speed camera will track landmarks on the stent and the distance between the marks will change as the mock vessel expands and contracts. A plurality of cameras may be necessary to give a full 360 degree view of the mesh tube.

At step 422, the tester is set to run at the predetermined parameters.

At step 424, when a break occurs then at step 426, the number of cycles to break is determined, and the tester continues to run. When a predetermined number of breaks have been met, then process is ended at step 428. The whole method is repeated with adjusted parameters to generate the data necessary to determine fatigue properties of the tested stent.

As described above, the fatigue-to-fracture testing methodology applies hyper-physiological loading conditions to the implantable medical device to cause a failure event to occur within a relatively short time frame. The loading conditions are then altered and the test is repeated on additional test articles of an implantable medical device. Some preferred embodiments of the foregoing method are described in detail below.

In some preferred embodiments, test articles of the implantable medical device is deployed into a set of mock vessels having a compliance of 2% per 100 mmHg when tested at typical physiological conditions. The mock vessels are then filled with liquid silicone, and the liquid silicone was allowed to drain from a first end of the lumens of each mock vessel to create the inner layer. The mock vessels are then filled with liquid silicone and allowed to drain from the second end of the lumens to create an additional inner layer. One or more of the mock vessels with test articles are then placed into a testing system such as described above, and the lumens are filled with a pressurized fluid with a pulsatile pressure at hyper-physiological conditions to induce failure of the test articles of the implantable medical device.

In some preferred embodiments of the method, the pulsatile pressure will be applied for a predetermined set of cycles and then the pressures are increased in a staircase method to cause failure. In a preferred embodiment of the method, the test articles are subjected to $10^6$ cycles at either 30 Hz or 60 Hz before the pressure is increased to the next level. In a preferred embodiment, the hyper-physiological pressure levels utilized are 500±40 mmHg, 500±100 mmHg, 500±200 mmHg, 500±300 mmHg, 500±400 mmHg, and 750±500 mmHg. In another preferred embodiment, the hyper-physiological pressure levels utilized are 500±150 mmHg, 500±200 mmHg, 500±250 mmHg, 500±300 mmHg, 500±400 mmHg, 500±400 mmHg, and 750±500 mmHg. The ± values indicate the range of the pulsatile pressure change during testing. During testing each test article is continuously or periodically checked for failure, and the cycles to failure are determined at varying levels of precision. When a test article fails it may be removed from the testing system or disconnected from the pulsatile pressure. In a preferred embodiment, the test articles are checked for failure at each change in the pressure settings. The pressures used in the iterations of the testing are selected to characterize the endurance limit of the implantable medical device using fatigue-to-fracture techniques. The increasing staircase method described in this paragraph may be used to determine the relevant pressure range for the fatigue-to-fracture testing for a specific implantable medical device.

In other preferred embodiments of the method, the pulsatile pressure will be applied for a predetermined set of cycles and the pressures are then decreased. In preferred embodiments, the hyper-physiological pressure levels utilized in the test are 750±500 mmHg, 500±450 mmHg, 500±425 mmHg, 500±400 mmHg, 500±300 mmHg, 500±200 mmHg, and 500±150 mmHg. In this method the test articles are subjected to each pressure level for $10^7$ cycles or until failure is detected. Each test article is intermittently checked for failure during testing cycle. In a preferred embodiment of this method, each test article is checked for failure after 100,000, 180,000, 320,000, 560,000, $10^6$, $1.8 \times 10^6$, $3.2 \times 10^6$, $5.6 \times 10^6$, and $10^7$ cycles. In other embodiments, the test articles may be checked for failure at higher or lower frequencies. The cycles and pressures at which failures occurred are recorded, and test articles that survived all testing pressures are considered "runout". The data collected by these methods may be used to characterize the endurance limit of the implantable medical device using known methods of analysis such as the Wöhler curve method described below.

In additional preferred embodiments, one or more additional mock vessels with test articles are placed into a testing system, and the lumens are filled with a pressurized fluid with a pulsatile pressure at one or more selected hyper-physiological conditions to induce failure of the test articles of the implantable medical device at a variety of hyper-physiological conditions. The pressures and frequencies used in the iterations of the testing may be selected to further characterize the endurance limit of the implantable medical device based on information collected in prior testing cycles. For example, pressure amplitudes between previously tested amplitudes may be tested to add further definition to a Wöhler curve.

In a preferred embodiment of the inventive method described above, known techniques for analyzing data collected during fatigue-to-fracture tests are utilized to characterize the endurance limit of an implantable medical device. One well known method of characterizing the endurance or stress limit of a device is a Wöhler curve such as that shown on FIG. 7. The depicted graph of the results of an exemplary fatigue-to-fracture test are depicted. The graph depicts the horizontal axis (abscissa) of cycles to failure versus the vertical axis (ordinate) of test pressure. This type of stress versus cycles graph may be used to produce a Wöhler curve to characterize the materials performance of a test article, in this case an implantable medical device.

In the depicted graph 700, the average cycles-to-failure 702, 704, 706, and 708 at each pressure are plotted. Runout values 710 and 712 may also be plotted to show that no failures occurred at certain pressures. A graph of the trend of the data points from the testing may be used to fit a curve 714 to the data, thus estimating the endurance limit 716 of the implantable medical device.

Figure 7:
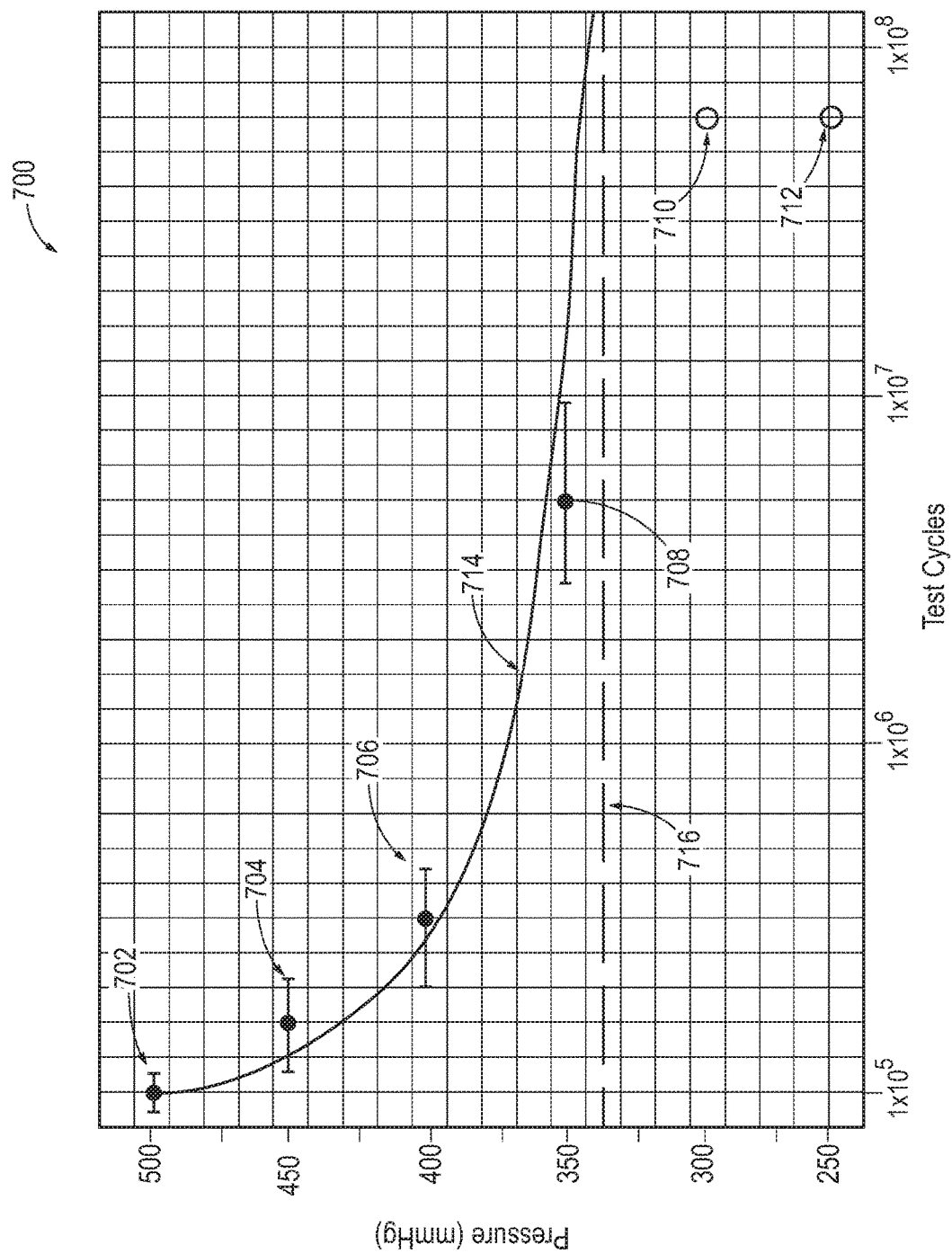
FIG. 7 is a depiction of a Wöhler curve used in fatigue-to-fracture testing analysis.

In the graph depicted in FIG. 7, the solid data points depict test iterations where the test articles failed. In the depicted graph, data point 702 depicts the average cycles to failure for the test articles at a mean test pressure of 500 mmHg. Similarly, data points 704, 706, and 708, represent the average cycles to failure for test articles at 450 mmHg, 400 mmHg, and 350 mmHg, respectively. Circle data points 710 and 712 depict test iterations in which the maximum number of cycles for the test was reached before the occurrence of any test article failures, which may also be referred to as a runout event.

The data points 702, 704, 706, and 708 may be used to construct a logarithmic curve 714 to fit the data. This logarithmic curve, or Wöhler curve, 714 helps characterize the horizontal asymptotic value 716 for stress (or in this case baseline pressure) below which a properly function article of the device will never fail. This asymptotic value 716 is sometimes referred to as the fatigue limit, the endurance limit, or the fatigue strength of a material. If the endurance limit value 716 is greater than the normal physiological loading conditions to which the implantable medical device will be subjected, then a properly manufactured article of the device should never fail during use.

In some embodiments of the fatigue-to-fracture methods described herein, average pressures of up to 2,500 mmHg may be utilized, with cyclic pressure differentials of ±500 mmHg or more at rates such as 30 Hz or 60 Hz.

Changes may be made in the above methods, devices and structures without departing from the scope hereof. Many different arrangements of the various components depicted, as well as components not shown, are possible without departing from the spirit and scope of the present invention. Embodiments of the present invention have been described with the intent to be illustrative and exemplary of the invention, rather than restrictive or limiting of the scope thereof. Alternative embodiments will become apparent to those skilled in the art that do not depart from its scope. Specific structural and functional details disclosed herein are not to be interpreted as limiting, but merely as a representative basis for teaching one of skill in the art to employ the present invention in any appropriately detailed structure. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A method for determining the endurance limit of an implantable medical device designed for implantation into a target human vessel, the method comprising the steps of:
   providing at least one mock vessel having a compliance that is lower than the normal compliance of the target human vessel;
   deploying one of at least one test article of the implantable medical device in a lumen of the at least one mock vessel;

applying a curable liquid to the lumen of the at least one mock vessel to form a liner layer over the at least one test article of the implantable medical device; and applying a high pressure pulsatile pressurization to the lumen of the at least one mock vessel at least until the occurrence of at least one failure event.

2. The method of claim 1, wherein the step of applying a curable liquid to the lumen of the at least one mock vessel comprises the steps of:

injecting the curable liquid into the lumen of each of the at least one mock vessel in a quantity sufficient to encapsulate the test article of the implantable medical device in a layer; and curing the curable liquid to form a solid liner layer.

3. The method of claim 2, further comprising the step of repeating the step of applying a curable liquid to the lumen of the mock vessel to form a second inner layer.

4. The method of claim 1 further comprising the steps of:

recording a data set including a pressure value and a number of cycles associated with each of the at least one failure event; and determining the endurance limit of the implantable medical device based on the data set.

5. The method of claim 1 wherein the implantable medical device is selected from the group consisting of a stent, a graft, and a stent-graft.

6. The method of claim 1, wherein the step of applying a high pressure pulsatile pressurization to the lumen of the at least one mock vessel at least until the occurrence of at least one failure event further comprises the steps of:

applying a high pressure pulsatile pressurization to the lumen of the at least one mock vessel for a first number of pressurization cycles;

inspecting each of the at least one test article for a failure;

repeating the steps of applying and of inspecting until a failure event is identified in at least one of the test articles or until a maximum number of pressurization cycles has been applied to the at least one mock vessel.

7. The method of claim 1 wherein the liner layer has a compliance that is higher than the normal compliance of the target human vessel.

8. A method for determining the endurance limit of an implantable medical device designed for implantation into a target human vessel, the method comprising the steps of:

providing at least one mock vessel having a compliance that is higher than the normal compliance of the target human vessel;

deploying at least one test article of the implantable medical device in a lumen of the at least one mock vessel;

applying a curable liquid to the lumen of the at least one mock vessel to form a liner layer over the at least one test article of the implantable medical device; and applying a high pressure pulsatile pressurization to the lumen of the at least one mock vessel at least until the occurrence of at least one failure event;

recording a data set including a pressure value and a number of cycles associated with each of the at least one failure event; and determining the endurance limit of the implantable medical device based on the data set.

9. The method of claim 8, wherein the step of applying a curable liquid to the lumen of the at least one mock vessel comprises the steps of:

injecting the curable liquid into the lumen of each of the at least one mock vessel in a quantity sufficient to encapsulate the test article of the implantable medical device in a layer; and curing the curable liquid to form a solid liner layer.

10. The method of claim 9, further comprising the step of repeating the step of applying a curable liquid to the lumen of the mock vessel to form a second inner layer.

11. The method of claim 8 wherein the implantable medical device is selected from the group consisting of a stent, a graft, and a stent-graft.

12. The method of claim 8, wherein the step of applying a high pressure pulsatile pressurization to the lumen of the at least one mock vessel at least until the occurrence of at least one failure event further comprises the steps of:

applying a high pressure pulsatile pressurization to the lumen of the at least one mock vessel for a first number of pressurization cycles;

inspecting each of the at least one test article for a failure;

repeating the steps of applying and of inspecting until a failure event is identified in at least one of the test articles or until a maximum number of pressurization cycles has been applied to the at least one mock vessel.

13. The method of claim 8 wherein the liner layer has a compliance that is higher than the normal compliance of the target human vessel.

14. A method for determining the endurance limit of an implantable medical device designed for implantation into a target human vessel, the method comprising the steps of providing a mock vessel having a compliance that is higher or lower than the normal compliance of the target human vessel;

deploying a test article of the implantable medical device into a lumen of the mock vessel;

filling the lumen of the mock vessel with a curable liquid;

allowing the excess of the curable liquid to drain from the lumen to form a cured inner layer;

applying a pulsatile pressurization to the lumen of the mock vessel using a fluid until the occurrence of a failure event.

15. The method of claim 14 further comprising the step of reducing the pressure of the pulsatile pressurization after a fixed number of cycles if a failure event has not occurred.

16. The method of claim 15 further comprising the step of recording a data set comprising the pulsatile pressurization and the number of cycles upon occurrence of a failure event.

17. The method of claim 16 further comprising the step of repeating the steps of claim 16 for a plurality of test articles of the implantable medical device in a plurality of mock vessels.

18. The method of claim 17 wherein the plurality of mock vessels have a compliance that is lower than the normal compliance of the target human vessel.

19. The method of claim 18 wherein the liner layer in the plurality of mock vessels has a compliance that is higher than the normal compliance of the target human vessel.

20. The method of claim 17 wherein the plurality of mock vessels have a compliance that is higher than the normal compliance of the target human vessel.

* * * * *